US006344488B1

United States Patent
Chenite et al.

(10) Patent No.: US 6,344,488 B1
(45) Date of Patent: Feb. 5, 2002

(54) TEMPERATURE-CONTROLLED PH-DEPENDENT FORMATION OF IONIC POLYSACCHARIDE GELS

(75) Inventors: Abdellatif Chenite, Kirkland; Cyril Chaput, Montreal, both of (CA); Christele Combes, St-Agne (FR); Amine Selmani, Laval; Fayrouze Jalal, Montréal, both of (CA)

(73) Assignee: Bio Syntech, Laval, CA (US)

( * ) Notice: Subject to any disclaimer, the term of this patent is extended or adjusted under 35 U.S.C. 154(b) by 0 days.

(21) Appl. No.: 09/250,066

(22) Filed: Feb. 12, 1999

Related U.S. Application Data (63) Continuation of application No. PCT/CA98/00326, filed on Apr. 6, 1998.

(51) Int. Cl.[7] ................. A61K 47/00; A61K 31/715; A01N 43/04; A61F 13/00; A61F 2/00

(52) U.S. Cl. ................. 514/777; 514/54; 514/55; 424/422; 424/423

(58) Field of Search ................. 514/777, 54, 55; 424/422, 423

(56) References Cited

U.S. PATENT DOCUMENTS

| | | |
|---|---|---|
| 4,185,618 A | 1/1980 | Corey |
| 4,391,909 A | 7/1983 | Lim |
| 4,474,769 A | 10/1984 | Smith |
| 4,647,536 A | 3/1987 | Mosbach |
| 4,659,700 A | 4/1987 | Jackson |
| 4,956,350 A | 9/1990 | Mosbey |
| 5,073,202 A | 12/1991 | Wallach et al. |
| 5,126,141 A | 6/1992 | Henry |
| 5,266,326 A | 11/1993 | Barry et al. |
| 5,422,116 A | 6/1995 | Yen et al. |
| 5,587,175 A | 12/1996 | Viegas et al. |
| 5,773,608 A * | 6/1998 | Yen .............................. 536/124 |
| 5,871,985 A * | 2/1999 | Aebischer .................... 435/178 |
| 5,944,754 A * | 8/1999 | Vacanti ........................ 623/11 |

FOREIGN PATENT DOCUMENTS

EP 94112944.7 8/1994 ............. C08L/5/08

OTHER PUBLICATIONS

CA Abstract, AN 1990:25365, Senoo et al, 1990.*
Ohya Y. et al. J. *Micro–encapsulation*, 10(1):1–9, 1993.
Zielinski B.A. et al. *Biomaterials*, 15(13): 1049–1056, 1994.
Back J.F. et al., *Biochemistry*, 18(23): 5191–5196.
Chung C.H. et al., *Calcif. Tissue Int.*, 51:305–311, 1992.
Bellows C.G. et al., *Bone and Mineral*, 17: 15–29, 1992.
Guo J. et al., *Connective Tissue Research*, 19: 277–297, 1989.
Li, X., *Biotechnol Appl. Biochem.*, 23: 269–271, 1996.

(List continued on next page.)

*Primary Examiner*—Russell Travers
*Assistant Examiner*—Shengjun Wang
(74) *Attorney, Agent, or Firm*—Nixon Peabody LLP (57) ABSTRACT

The present invention relates a temperature-controlled pH-dependant formation of ionic polysaccharide gels, such as chitosan/organo-phosphate aqueous systems, and methods of preparation thereof. While chitosan aqueous solutions are pH-dependant gelating systems, the addition of a monophosphate dibasic salt of polyol or sugar to a chitosan aqueous solutions leads to further temperature-controlled pH-dependant gelation. Solid organo-phosphate salts (1–20% w/v) are added and dissolved at low temperature (10° C.) within 0.5 to 4.0% w/v chitosan in aqueous acidic solutions. Aqueous chitosan/organo-phosphate solutions are initially stored at low temperatures (4° C.), then endothermally gelated within the temperature range of 30 to 60° C. Chitosan/organo-phosphate solutions rapidly turn into gels at the desired gelation temperature. Gelation can be ex vivo within any receivers or molds, or in situ in animals or humans (in vivo) so as to fill a tissue defect or cavity.

28 Claims, 6 Drawing Sheets

OTHER PUBLICATIONS

Gupta S. et al., *The International Journal of Artificial Organs*, 16:3, 155–163, 1993.

Matthew H.W.T. et al., *Journal of Pediatric Surgery*, 28:11, 1423–1428, 1993.

Rao, S. Bhaskara et al., *Journal of Biomedical Materials Research*, 34: 21–28, 1997.

Muzzarelli R. et al., *Biomaterials*, 9: 247–252, 1988.

Muzzarelli, R.A.A. et al., *Biomaterials*, 15:13, 1075–1081, 1994.

Calvo P. et al., *Colloid Polym. Sci.*, 275:46–53, 1997.

Aspden T.J. et al., *European Journal of Pharmaceutical Sciences*, 4:23–31, 1996.

* cited by examiner

FIG_1

TEMPERATURE-CONTROLLED PH-DEPENDENT FORMATION OF IONIC POLYSACCHARIDE GELS

This application is a continuation of PCT/CA98/00326 filed Apr. 6, 1998 designating the United states and claiming priority of Canadian patent application number 2,212,300 filed Aug. 4, 1997.

FIELD OF THE INVENTION

The present invention relates to a temperature-controlled pH-dependant formation of ionic polysaccharide gels, such as chitosan/organo-phosphate aqueous systems, and methods of preparation thereof.

BACKGROUND OF THE INVENTION

Chitosan is a commercially available inexpensive polymer, a derivative of chitin or poly(N-acetyl-glucosamine) materials. Chitosan is mainly composed of D-glucosamine units that are generated through catalyzed N-deacetylation of chitin, an insoluble biopolymer extracted from hard shells of marine living animals (fishes, crustaceans, shrimps, crabs . . . ) or synthesized by natural organisms (zygomycete, fungi . . . ). Chitosan is expected to have good viscoelastic properties, and has adequate tissue compatibility and biodegradability which renders it ideal for bioactive and resorbable implants. Poly-D-glucosamine chains are also known to potentially attach a large number of proteoglycan molecules and coexist with fibrous collagens to form aqueous gels. It is believed that the role of proteoglycans within the gel is to retain water and supply appropriate viscoelasticity. Resulting extracellular matrices are expected to offer compatible environments for cellular proliferation and tissue formation, especially for skin, ligament, bone and cartilage cells. As a consequence, chitosan attracts great interest for scaffolding or supporting materials of bioengineered artificial tissues.

Moreover, chitin and partially-acetylated chitosan derivatives have been extensively investigated for therapeutic substances or implantable materials. Biocompatibility of chitosan-based materials has been evaluated specifically for blood, wounds and bone. Immunological and genotoxic activities as well as stimulatory effects on macrophagic action have been also studied with various chitosan materials.

Chitosan and its derivatives has been widely explored for drug delivery system through gels (Ohya Y. et al. (1993) *J. Micro-encapsulation*, 10(1):1–9). Peptides delivery with chitosan was proposed to be effected nasally. Cationic colloidal drug carriers were proposed from chitosan-polycaprolactone systems. Wound healing and reconstructive devices made of chitosan materials have been proposed for open or corneal wounds, periodontal tissues and skin. Chitosan was specially evaluated in bone and dura matter and as an hemostatic.

Entrapment of living biologicals (cells, enzymes, etc . . . ) have been investigated with different chitosan products, however, in nearly all cases, living cells have been encapsulated within alginate/chitosan microbeads. Encapsulation of chondrocytes (cartilage cells) were proposed within calcium-alginate/chitosan beads.

Gelation of chitosan through polyphosphates has been promoted for encapsulating cells such as neural or musculo-squeletal tissues. Generally, chitosan in an acid/water medium was loaded with cell suspensions, and the resulting mixture was dropped in a buffered penta-sodium tri-polyphosphates so as to form cell-loaded chitosan beads and capsules. Entrapment of neural cells within polyphosphate-gelated chitosan beads has led to good cellular viability but low proliferation rate (Zielinski B. A. et al. (1994) *Biomaterials*, 15(13) :1049–1056). No large or specific three-dimensional shaped materials were proposed (Zielinski B. A. et al. (1994) *Biomaterials*, 15(13) :1049–1056). Polysaccharide capsules have been proposed for entrapping physiologically active cells such as Langerhans Islets (U.S. Pat. No. 4,391,909). Chitosan/hydrochloride cisplatin mixture were cross-linked and proposed as drug delivery systems.

Chitosan derivatives have been incorporated in numerous carrier composition or drug formulation. Chitosan materials such as wound filling materials or contraceptive products were also proposed (U.S. Pat. Nos. 4,956,350 and 4,474,769). Chitosan gels were again reported as supports for immobilizing and encapsulating living biomaterials such as cells, bacteria and fungi (U.S. Pat. No. 4,647,536). Ophthalmic drug delivery systems made of chitosan were also proposed for in situ gelating and forming (U.S. Pat. No. 5,422,116).

In U.S. Pat. No. 4,659,700, chitosan gels were prepared from glycerol/acid/water systems as biodegradable carriers for drug delivery. The resulting chitosan gels were reported to remain quite stable, keeping intact their three-dimensional shape for long periods and over a wide range of temperatures, particularly between 4 and 40° C. Gels and gel-like materials were processed by dissolving 1.0 to 4.0% w/v chitosan within acid-water-glycerol solutions wherein acetic, formic or propionic acid and 10–90% glycerol proportions are used preferentially, and by neutralizing with liquid bases such the sodium, ammonium and potassium hydroxides or ammonia vapors. The pH of the resulting chitosan-glycerol gel materials is about pH 7.0. After neutralization, the resultant mixtures turn into gels upon standing, such gels resulting apparently from the interaction of chitosan, glycerol and water. No free glycerol or water were reported as being apparent. It must be noted, however, that such three-dimensionally shaped chitosan-glycerol gels will occur only when the solution is previously neutralized with a base. One-piece three-dimensional gels can be molded easily as well as gel-like membranes. The role of the glycerol component and chitosan-glycerol interactions is not elucidated.

In situ formed gels were also proposed with ionic polysaccharides in U.S. Pat. No. 5,587,175. A composition can be used as a medical device for drug delivery, the application of a diagnostic agent, or the prevention of post-operative adhesions, and is composed an aqueous liquid vehicle which is capable of being gelled in situ. It includes at least one ionic polysaccharide, at least one film forming polymer, and a medicament or pharmaceutical agent, water, and optionally, a counter-ion capable of gelating the ionic polysaccharide (U.S. Pat. No. 5,587,175). However, the gelation is reached by interaction between the ionic polysaccharide and the film-forming polymer, or by counter-ion induced cross-linking of the ionic polysaccharide. Other in situ forming gels are based upon polyoxyalkylene composition (U.S. Pat. No. 4,185,618) or polyoxyalkylene/polysaccharide mixture (U.S. Pat. No. 5,126,141) or alginate/cation mixture in situ (U.S. Pat. Nos. 4,185,618 and 5,266,326).

It would be highly desirable to be provided with a temperature-controlled pH-dependant formed polysaccharide gel which could be used to encapsulate cells and cellular material while retaining their biological activity.

It would be highly desirable to be provided with such a polysaccharide gel which would retain its solid or gel state at the physiological temperature or 37° C.

SUMMARY OF THE INVENTION

One aim of the present invention is to provide a temperature-controlled pH-dependant formed polysaccharide gel which could be used to encapsulate cells and cellular material while retaining their biological activity.

Another aim of the present invention is to provide a polysaccharide gel which would retain its solid or gel state at the physiological temperature or 37° C.

Another aim of the present invention is to provide a method for the preparation of such a polysaccharide gel.

In accordance with the present invention there is provided a polysaccharide based gel which comprises:
- a) 0.1 to 5.0% by weight of chitosan or a chitosan derivative; and
- b) 1.0 to 20% by weight of a salt of polyol or sugar selected from the group consisting of mono-phosphate dibasic salt, mono-sulfate salt and a mono-carboxylic acid salt of polyol or sugar;

wherein said gel is induced and stable within a temperature range from 20 to 70° C. and is adapted to be formed and/or gelated in situ within a tissue, organ or cavities of an animal or a human.

The salt may be any of the following or in any of the following combination:
- a) a mono-phosphate dibasic salt selected from the group consisting of glycerol, comprising glycerol-2-phosphate, sn-glycerol 3-phosphate and L-glycerol-3-phosphate salts;
- b) a mono-phosphate dibasic salt and said polyol is selected from the group consisting of histidinol, acetol, diethylstilbestrol, indole-glycerol, sorbitol, ribitol, xylitol, arabinitol, erythritol, inositol, mannitol, glucitol and a mixture thereof;
- c) a mono-phosphate dibasic salt and said sugar is selected from the group consisting of fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose, hexose, methylthio-ribose, methylthio-deoxy-ribulose, and a mixture thereof;
- d) a mono-phosphate dibasic salt and said polyol is selected from the group consisting of palmitoyl-glycerol, linoleoyl-glycerol, oleoyl-glycerol, arachidonoyl-glycerol, and a mixture thereof; and
- e) glycerophosphate salt is a selected from the group consisting of glycerophosphate disodium, glycerophosphate dipotassium, glycerophosphate calcium, glycerophosphate barium and glycerophosphate strontium.

A preferred gel in accordance with one embodiment of the present invention is selected from the group consisting of chitosan-β-glycerophosphate, chitosan-α-glycerophosphate, chitosan-glucose-1-glycerophosphate, and chitosan-fructose-6-glycerophosphate.

The solid particulate or water-soluble additives may be incorporated within said polysaccharide gel prior to the gelation.

The drugs, polypeptides or non-living pharmaceutical agents may be incorporated within said polysaccharide gel prior to the gelation.

The living microorganisms, plant cells, animal cells or human cells may be encapsulated within said polysaccharide gel prior to the gelation.

The gel may be formed in situ sub-cutaneously, intra-peritoneally, intra-muscularly or within biological connective tissues, bone defects, fractures, articular cavities, body conduits or cavities, eye cul-de-sac, or solid tumors.

The gel of the present invention may be used as a carrier for delivering pharmaceutical agents in situ.

In accordance with the present invention there is also provided a method for producing a polysaccharide gel solution of the present invention, which comprises the steps of:
- a) dissolving a chitosan or a chitosan derivative within an aqueous acidic solution of a pH from about 2.0 to about 5.0 to obtain an aqueous polysaccharide composition having a concentration of 0.1 to 5.0% by weight of a chitosan or of a chitosan derivative;
- b) dissolving 1.0 to 20% by weight of a salt of polyol or sugar, wherein said salt is selected from the group consisting of mono-phosphate dibasic salt, mono-sulfate salt and a mono-carboxylic acid salt, in said aqueous polysaccharide composition of step a) to obtain a polysaccharide gel solution, wherein said polysaccharide gel has a concentration of 0.1 to 5.0% by weight of a chitosan or a chitosan derivative, and a concentration of 1.0 to 20% by weight of a salt of a polyol or sugar, and has a pH from about 6.4 to about 7.4.

This method may further comprises a step c) after step b),
- c) heating said polysaccharide gel solution at a solidifying temperature ranging from about 20° C. to about 80° C. until formation of a polysaccharide gel.

A pharmaceutical agent may be added to the polysaccharide gel solution of step b).

The method may further comprises a step i) after step b),
- i) dispensing for gelation the polysaccharide gel solution into a desired receiver, either in a mold or within a tissue, organ or body cavity.

The aqueous acidic solution may be prepared from organic or inorganic acids selected from the group consisting of acetic acid, ascorbic acid, salicylic acid, phosphoric acid, hydrochloric acid, propionic acid, formic acid, and a mixture thereof.

The polysaccharide gel solution may be kept in a stable ungelled liquid form at a temperature ranging from about 0° C. to about 20° C.

The solidifying temperature is ranging from about 37° C. to about 60° C., preferably about 37° C.

The molecular weight of chitosan is ranging from about 10,000 to 2,000,000.

The polysaccharide gel is thermoirreversible or thermoreversible by adjusting the polysaccharide gel pH, when the pH of said polysaccharide gel solution is >6.9, or when the pH of said polysaccharide gel solution is <6.9.

The solid particulate additives may be added to the polysaccharide gel solution of step b).

The polysaccharide gel solution may be introduced within an animal or human body by injection or endoscopic administration, and gelled in situ at a temperature of about 37° C.

In accordance with the present invention there is also provided the use of the polysaccharide gel for producing biocompatible degradable materials used in cosmetics, pharmacology, medicine and/or surgery.

The gel may be incorporated as a whole, or as a component, into implantable devices or implants for repair, reconstruction and/or replacement of tissues and/or organs, either in animals or humans.

The gel may be used as a whole, or as a component of, implantable, transdermal or dermatological drug delivery systems.

The gel may be used as a whole, or as a component of, opthalmological implants or drug delivery systems.

The gel may be used for producing cells-loaded artificial matrices that are applied to the engineering and culture of bioengineered hybrid materials and tissue equivalents.

The loaded cells may be selected from the group consisting of chondrocytes (articular cartilage), fibrochondrocytes (meniscus), ligament fibroblasts (ligament), skin fibroblasts (skin), tenocytes (tendons), myofibroblasts (muscle), mesenchymal stem cells and keratinocytes (skin).

The cells-loaded gel and derived products are devoted to the culture and engineering of artificial articular cartilage and cartilaginous tissues and organs, either for surgical or laboratory testing applications.

The cells-loaded gel and derived products are devoted to the processing and engineering of living artificial substitutes for ligaments, tendons, skin, bone muscles and any metabolic organs, either for surgical or laboratory testing applications.

The cells-loaded gel and derived products are applied as living substitutes for the replacement of articular cartilages, fibrocartilages, cartilaginous organs, ligaments, tendons, bone tissues or skin.

The cells-loaded hydrogel is gelated in situ to induce an ectopic formation of fibrocartilage-like or cartilage-like tissues.

In accordance with the present invention there is also provided the use of loaded polysaccharide gel as injectable or implantable gel biomaterials which act as supports, carriers, reconstructive devices or substitutes for the formation in situ of bone-like, fibrocartilage-like or cartilage-like tissues at a physiological location of an animal or a human.

The polysaccharide gel solution may be used for producing a derived gel or hydrogel by 1) incorporating and dissolving at least one complementary polymer within said polysaccharide gel solution, and 2) by allowing said polysaccharide and complementary polymer to interact for a sufficient period of time to turn into a clear three-dimensional gel within a temperature range between 20° C. to 60° C.

The complementary polymer is a non-ionic water-soluble polysaccharide or a hydroxyalkyl cellulose.

For the purpose of the present invention the following terms and expressions are defined below.

The term "polysaccharide gel solution" is intended to mean a polysaccharide solution in a stable ungelled liquid form at a temperature ranging from about 0° C. to about 15° C. which can be gelated or changed to a gel state when heated at the gelating temperature.

The term "gelating temperature" is intended to mean any temperature ranging from about 20° C. to about 80° C., preferably between 37° C. to about 60° C., and more preferably at about the physiological temperature or 37° C.

The expression "salts of polyols or sugars" is intended to mean mono-phosphate di-basic salts, mono-sulfate salts-and mono-carboxylic acid salts of polyols or sugars.

The present invention include method of forming different gelated materials, those materials being either molded (customized shapes, tubes, membranes, films . . . ) or formed in situ within biological environments (filling of tissue defects).

In a preferred embodiment, the chitosan/organo-phosphate aqueous solution has a pH above the pKa of chitosan and turn into solid gel upon thermal stimulation. This polysaccharide gel can be used as a carrier for drugs or as a non-living therapeutics delivery system, as substituting materials for tissues and organs and as encapsulants for living cells or microorganisms. Chitosan/organo-phosphate gel matrices are rapidly formed at temperatures between 30 to 60° C. Chitosan/organo-phosphate aqueous systems are used as injectable filling materials, injected and gelated in situ for filling and repairing tissue defects.

Glycerol-2-phosphate, glycerol-3-phosphate and glucose-1-phosphate based salts are the preferred disclosed salts in accordance with the present invention.

Chitosan/polyol- or sugar-phosphate and chitosan/polyol- or sugar-sulfate gels can be applied to surgical reconstructive and regeneration uses and drug delivery purposes. They provide thermally reversible or irreversible bioerodible polymeric gels with biologically well-known and compatible components for a broad range of medical/biotechnological applications.

DETAILED DESCRIPTION OF THE INVENTION

Chitosan is dissolved in acidic aqueous solutions so as to obtain clear aqueous chitosan solutions having pH levels within the range 4.3 to 5.6. The chitosan solutions can be sterilized through filtering or steam-autoclaving, and stored at low positive temperature (4° C.). The organo-phosphate component is added to the chitosan solution, preferably at low positive temperature (40° C.), then the aqueous chitosan/organo-phosphate mixture is gelated thermally, through an endo-thermal mechanism, within the temperature range from 30 to 60° C. Once formed the resulting chitosan/organo-phosphate gels are thermally stable upon heating even up to 180° C. (in autoclave), particularly in cell culture medium. Bioencapsulation within chitosan/organo-phosphate gels is obtained by incorporating the living cells within the ungelated aqueous chitosan/organo-phosphate solution at a low temperature (4° C.). Then the temperature of the resulting mixture chitosan/organo-phosphate/cells is raised to and maintained at 37° C. where the gelation occurs in ~1 hour. organo-sulfates or mono-carboxylic acid salt of polyols or sugars play a similar role than organo-phosphates.

chitosan and its derivatives are relatively inexpensive and commercially available materials and represent an attractive group of biocompatible and degradable polymers. They have solid or solution properties which can be modified by changing their chemical composition and/or physico-chemical characteristics. The deacetylation degree and molecular weight have been shown to greatly influence the solution properties, enzymatic degradability and biological activity. Chemical modifications, for instance, have been proposed to neutralize or modify chitosan chains by incorporating carboxylic acid, acetate, glutamic acid, carboxymethyl or sulfate groups. Chemical cross-linking (anhydride, glutaraldehyde, glutamate succinimide-PEG . . . ) of chitosan macromolecules induces covalent bonds to create branched or grafted networks.

Physical gelation of chitosan and its derivatives can be obtained through different techniques:
a) neutralization (NaOH, KOH, $NH_4OH$ . . . ) which induces hydrogen bonding between chitosan chains;
b) ionic complexation with divalent anions (borate, molybdate, polyphosphate, sulfate salts and sulphated macromolecules . . . ) which induces pure electrostatic interactions;
c) complexation with anionic surfactants (sodium alkyl sulfate . . . ) which induces electrostatic interactions and surfactant-surfactant hydrophobic interactions.

In accordance with the present invention there is proposed a new gelation mechanism that combines hydrogen bonding, electrostatic interactions and chitosan-chitosan hydrophobic interactions. It can only be achieved through complex interactions between chitosan macromolecules, water molecules and mono-phosphate dibasic salts of polyols or sugars.

Polyols are frequently added to compositions for improving gel properties. Sorbitol and mannitol are currently used as tonicity enhancing agents. Glycerol and polyethylene glycol are proposed as plasticizers. Polyols (-ol: glycerol, sorbitol . . . ) and sugars (-ose: fructose, glucose, galactose . . . ) were used as thermal stabilizing Agents for proteins in solutions (Back J. F. et al. (1979) *Biochemistry*, 18(23):5191–5196). Depending on the selected molecules, they were found to make or break structuring of water, create hydrogen bonding, electrostatic or hydrophobic interacting, and present endothermic transitions (Back J. F. et al. (1979) *Biochemistry*, 18(23):5191–5196). Polyols and sugars stabilize proteins to heat denaturation through their structuring effect on water and the strengthen of hydrophobic interactions.

Beta-glycerophosphate disodium or calcium salt, or glycerol-2-phosphate disodium or calcium salt, is a well studied molecule in biological sciences. It is considered as a substrate for alkaline phosphatase (AL). glycerophosphate is widely used as a cell culture medium supplement for culturing cells isolated from musculo-skeletal tissues, and has been shown to induce or maintain the synthesis of specific matrix components when delivered to bone/cartilage cells in culture (Chung C.-H. et al. (1992) *Calcif. Tissue Int.*, 51:305–311; Bellows C. G. et al. (1992) *Bone and Mineral*, 17:15–29). Gelation of chitosan will occur with any grade or purity glycerophosphate while encapsulation of living biologicals would require cell culture tested glycerophosphate. Alpha-glycerophosphate disodium or calcium salt, or glycerol-3-phosphate disodium or calcium salt, is also an organic salt of biological importance (Chung C.-H. et al. (1992) *Calcif. Tissue Int.*, 51:305–311). Glycerophosphate salts are precipitated from glycerophosphoric acids which are obtained through the hydrolysis of lecithin, a well-know biological molecule and phosphatides of eggs, soybean and fishes. Glycerophosphoric acids are present under two isomeric structures, the alpha and beta, wherein the beta-glycerophosphoric acid is optically inactive and the alpha-glycerophosphoric acid is optically active. Glycerophosphoric acid is physiologically active compound, being involves in the catabolism of carbohydrates. Glycerophosphate dehydrogenase was also found active in nerve tissues while glycerophosphate was reported to accelerate the rate of decolonization of methylene blue by guinea pig nerves. Alpha-glycerophosphate interacts with pyruvic acid through oxidation-reduction reactions for producing lactic acid in fresh muscle extracts. Glycerophosphoric acid is currently available under disodium, calcium, magnesium, dipotassium, strontium and barium salts, having a relatively strong basic character. Both alpha- and beta-glycerophosphate salts are inexpensive readily available sources of organic mono-phosphate dibasic salts among the polyol or sugar phosphate salts.

Solubilization of chitosan in aqueous solutions requires the protonation of the amine groups of the chitosan chains which is reached within acidic aqueous solutions having a pH ranging from 3.0 to 5.0. When solubilized, chitosan remains soluble until a pH about 6.2. Neutralization of acidic chitosan solutions by alkali results in a pH increase as well as a de-protonation of the amine groups. Neutralization of acidic chitosan solutions to a pH above the pKa of chitosan at about 6.3–6.4 results in OH—HN and O—HN interchains and water-chitosan hydrogen bonds which induce a hydrated three-dimensional network, a chitosan gel. At pH above 6.3–6.4, chitosan solutions result systematically into chitosan gels at a normal temperature range (0–60° C.). However, admixing of an organo-phosphate to a chitosan aqueous solutions increases the pH of the chitosan/organo-phosphate solutions which remain ungelled and liquid for long periods of time even at pH above 6.5, and up to 7.2. This neo-neutral chitosan/organo-phosphate aqueous solutions (pH 6.5–7.2) will gelate when stimulated by an adequate temperature. The time of gelation is controlled by the temperature. For example, a chitosan/organo-phosphate solution which gelates in about 30 minutes at 37° C., needs only about 2 minutes at 60° C. to form a gel.

Figure 1:
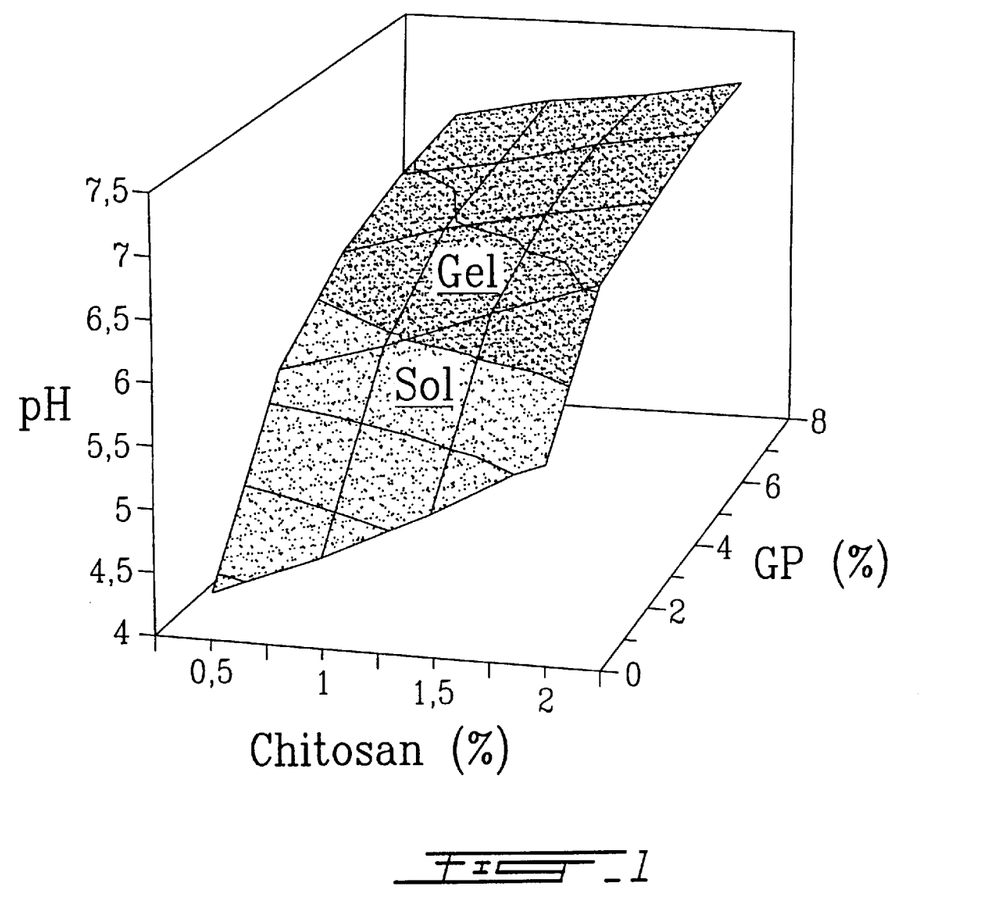
FIG. 1 illustrates the occurrence of thermally-controlled Sol to Gel transition (gel formation) dependent upon the pH of the chitosan/glycerophosphate aqueous solution characterized by the chitosan concentration (% by weight), the glycerophosphate concentration (% by weight) and the pH of the chitosan/glycerophosphate aqueous solution.
Figure 2:
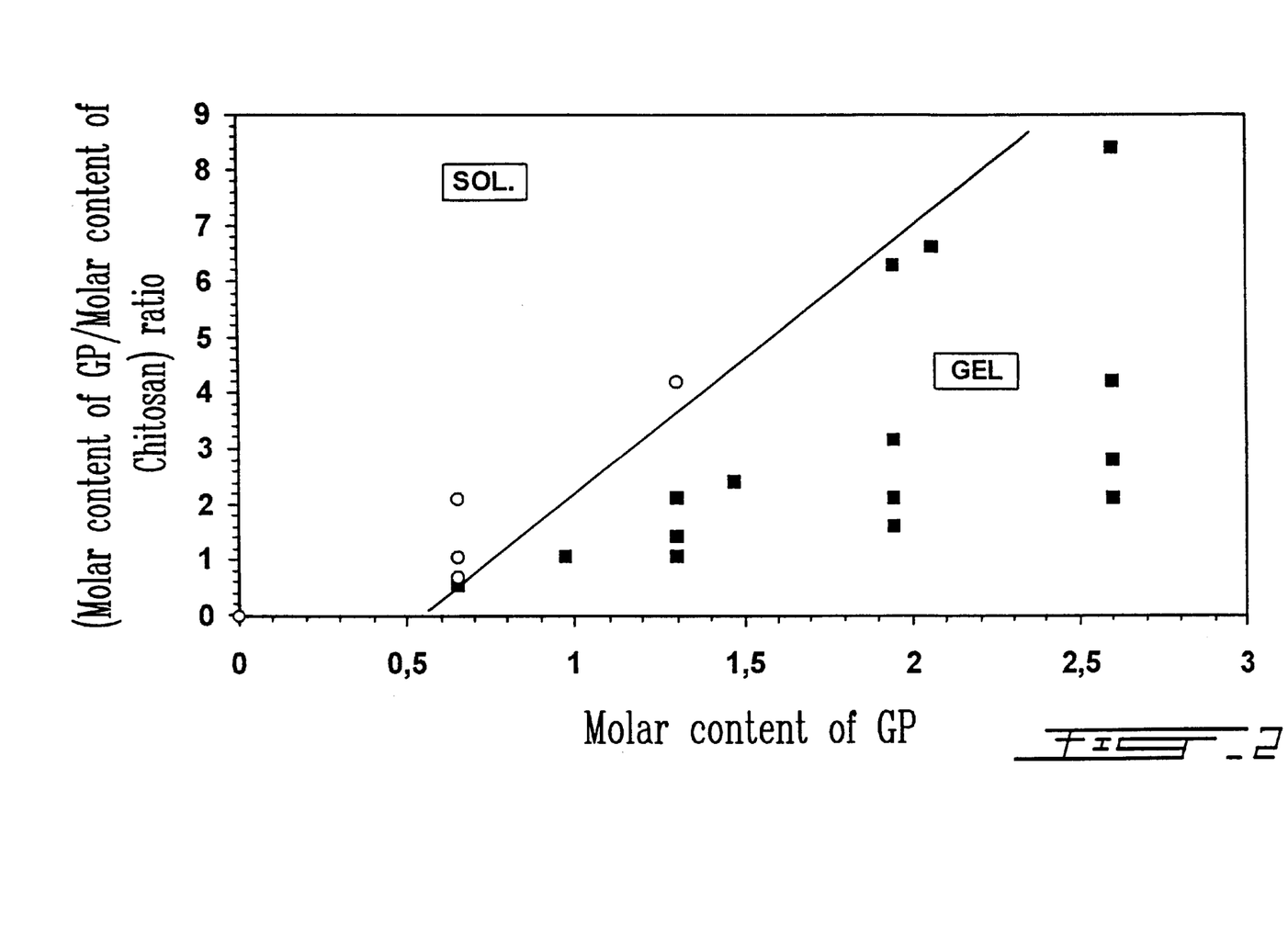
FIG. 2 illustrates the Sol/Gel diagram for the chitosan/glycerophosphate systems presented as a relationship between the molar content in glycerophosphate and the ratio of the molar content of glycerophosphate by the molar content of glucosamine units.
Figure 3:
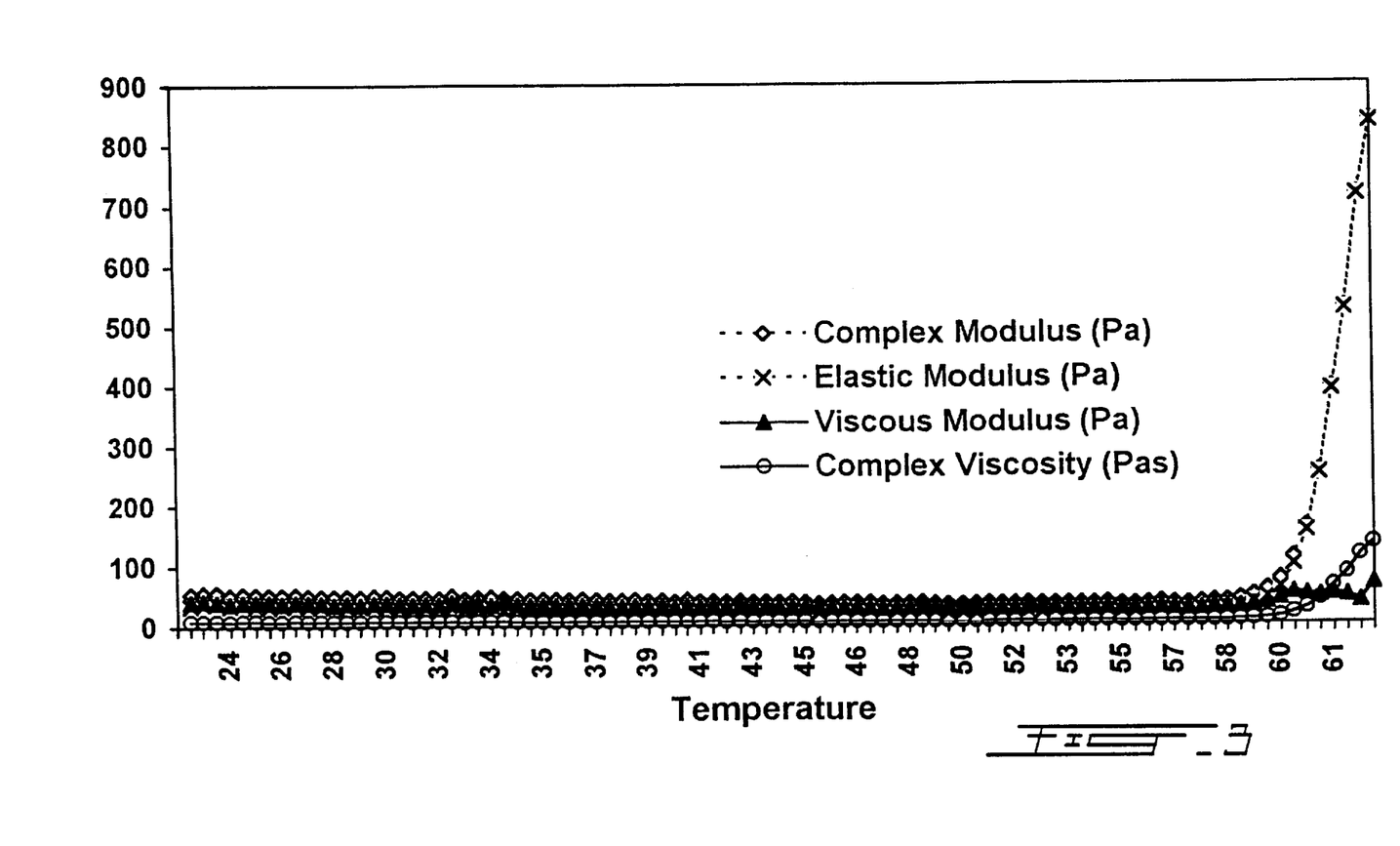
FIG. 3 illustrates the Sol to Gel transition (Gel formation) induced by heat and followed versus the temperature by rheologic measurement of the modulus and viscosity parameters.

The mechanism of gelation as well as the gel characteristics have been expected to be similar for all chitosan/organo-phosphate systems. Thus, the gelation of chitosan/β-glycerophosphate solutions which has been investigated in more details can be considered as typical example. The results indicating the pH-dependence and the temperature-dependence of the gelation for chitosan/β-glycerophosphate solutions are summarized in the sol-gel diagrams shown in FIGS. 1 and 2. In addition to the gel strength, the rheological experiments represented in FIG. 3, show unambiguously that the gelation of chitosan/β-glycerophosphate solutions occur upon heating. The changes in modulus which appear at about 60° C. are symptomatic of the Sol to Gel transition and Gel formation. This temperature for gel formation will be dependent upon the solution characteristics and heating rate (energy of activation required).

Figure 4A:
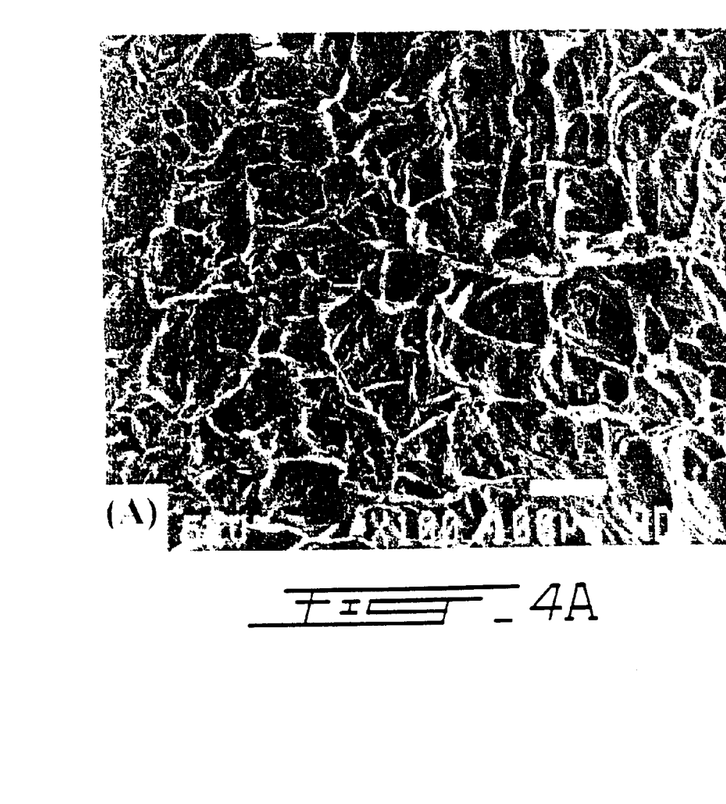
FIG. 4 illustrates the microstructures of chitosan/glycerophosphate gels formed in vitro viewed as observed by Scanning Electron Microscopy on gel samples that have been freeze-dried at −30° C. and during 8 hours.
Figure 4B:
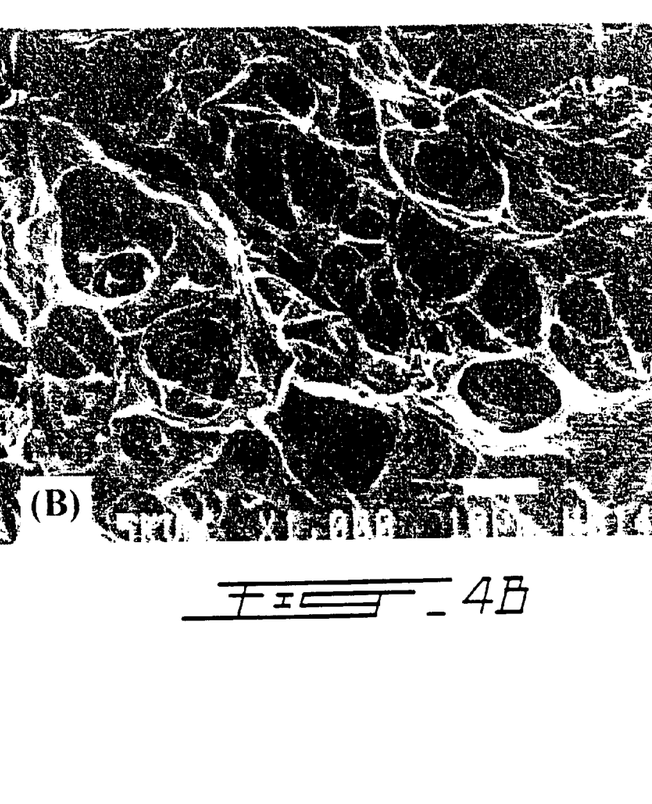

The porous structure of chitosan/β-glycerophosphate gels has been evidenced by Scanning Electron Microscopy as shown in FIG. 4. The gels have a typical microstructure with chambers about 100 microns and pores of about 10 microns. Their microstructure differ from those observed on chitosan gels processed by simple neutralization wherein a lamellar architecture was present.

Figure 5A:
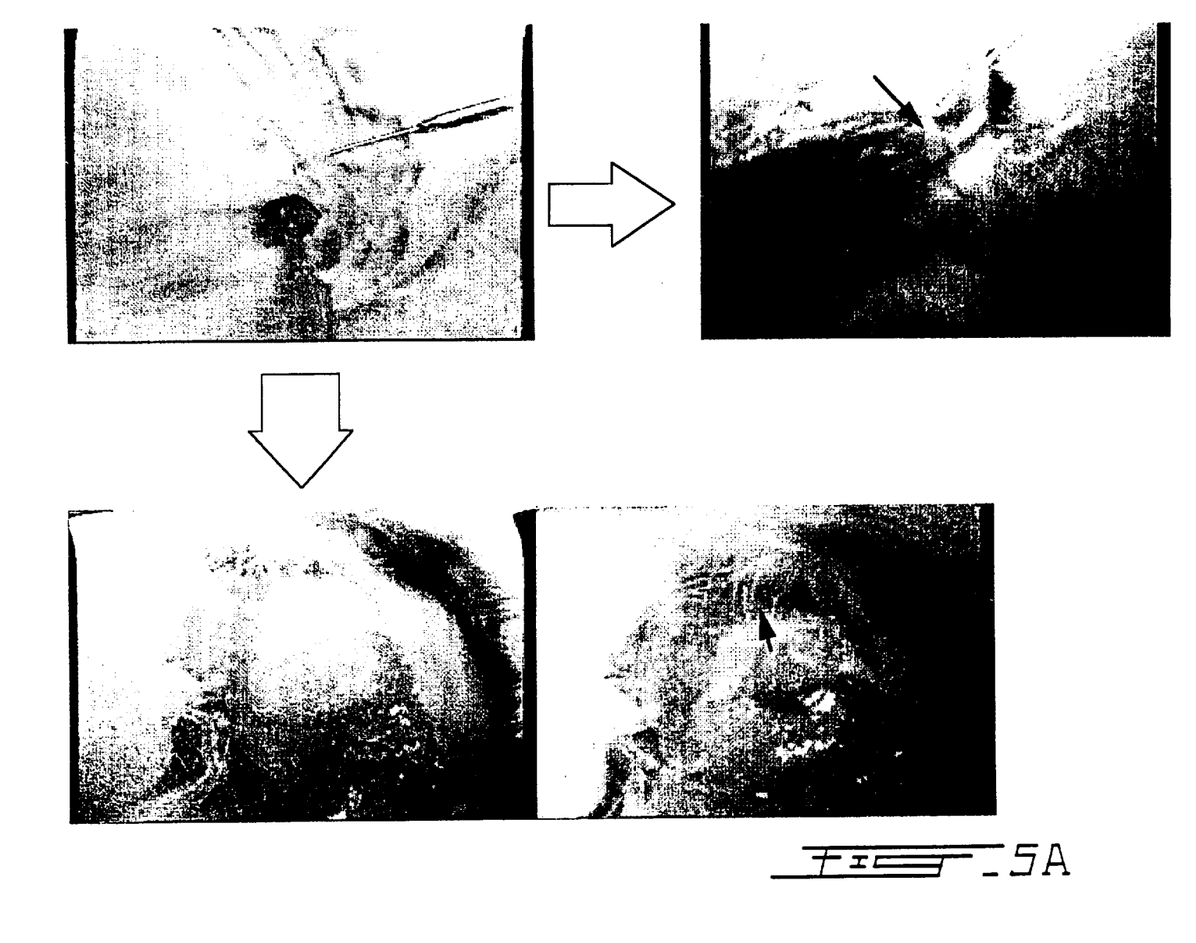
FIG. 5 illustrates chitosan/glycerophosphate solutions which are injected in rabbits, subcutaneously and intraarticularly in legs or subcutaneously at the torso, and allowed to gelate in situ at the body temperature.
Figure 5B:
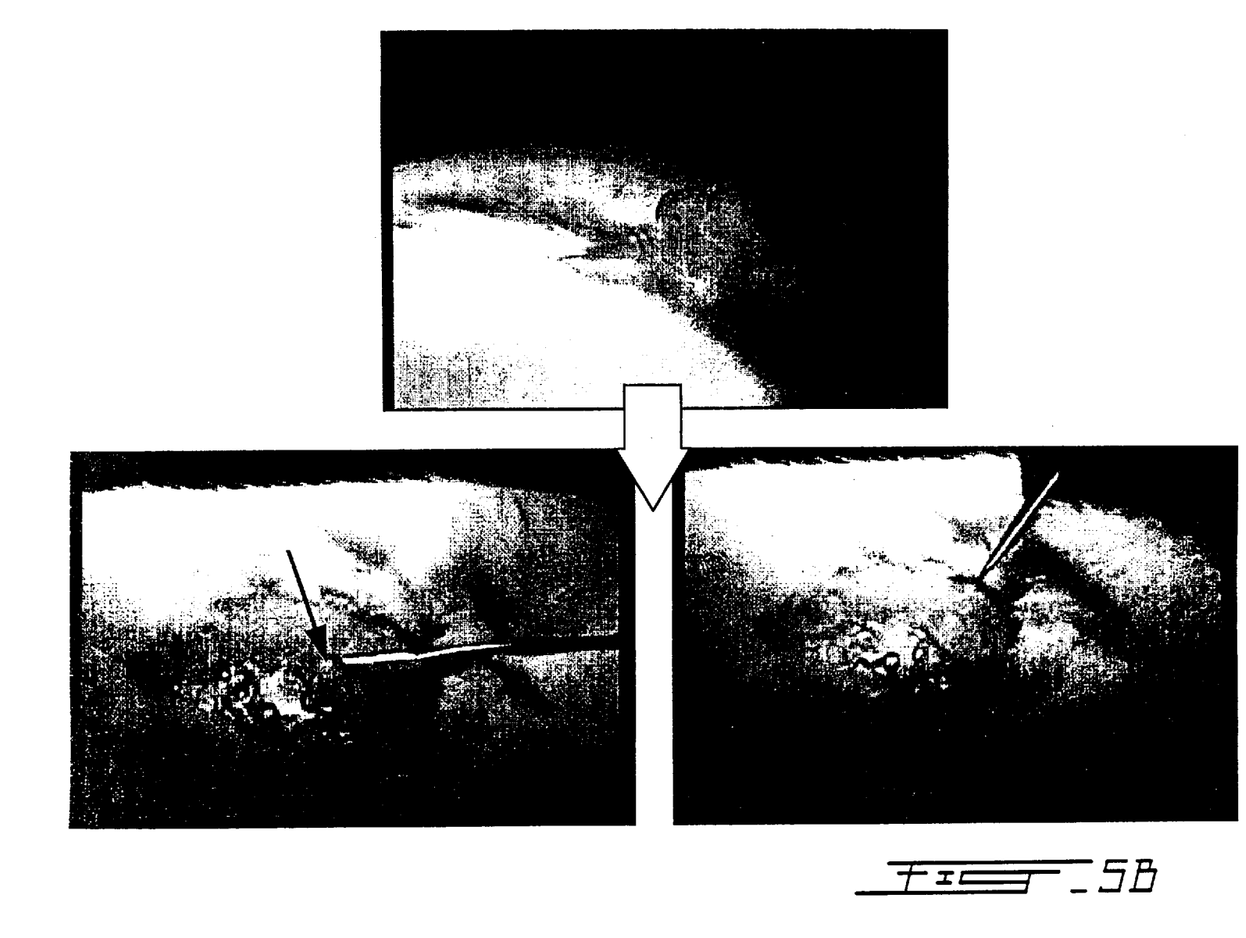

Another important characteristic is related to the injectability and in vivo gelation of chitosan/β-glycerophosphate solutions. Injections and gels are typically shown on FIGS. 5A and 5B. Black arrow in FIG. 5A shows the gel formed in situ at the knee joint intraarticular zone between the collateral ligament and the patellar tendon. The other gel is formed sub-cutaneously between the skin and leg muscles. Black arrow in FIG. 5B shows the gels formed subcutaneously in situ at the torso region.

In chitosan/organo-phosphate gels, organo-phosphate anions contribute to the cross-linking of chitosan macromolecule chains, but not in the same way as the pure ionic cross-linking that takes place during the gelation of chitosan by inorganic divalent anions, such as sulfate, oxalate, phosphate or polyphosphate (pyrophosphates, metaphosphates or tripolyphosphates). A chitosan aqueous solution turns into gel instantaneously in presence of inorganic divalent anions and independently of the solution pH value. Furthermore, the elevation of temperature constitutes an unfavorable factor for the gelation of this kind of systems. In contrast, the gelation of chitosan/organo-phosphate solution depends on both, the final pH of chitosan/organo-phosphate solution and the temperature. Every solution of chitosan/organo-phosphate can not be gelled, at any temperature, as long as its pH remains below 6.45, and every solution of chitosan/organo-phosphate with pH above 6.45 can be prepared at 20° C., without immediate gelation and can be stored for long time at 4° C. without turning to gel. At 37° C. only the chitosan/organo-phosphate solutions with pH above 6.9 can be gelled more or less rapidly. It is expected that the presence of organo-phosphate molecules in chitosan solutions directly affects electrostatic interactions, hydrophobic interactions and hydrogen bonds of chitosan chains. Thus, the main interactions involved in the formation of chitosan/organo-phosphate gels become essentially: 1) chitosan/chitosan interchain hydrogen bonding (CHITOSAN-CHITOSAN); 2) chitosan/organo-phosphate electrostatic attractions between the ammonium groups of macromolecule chains and the phosphate group of organo-phosphate molecules (CHITOSAN-PHOSPHATE); 3) chitosan-chitosan hydrophobic interactions induced through the structuring action of the polyol or sugar parts on water molecules. The structuring action of the polyol parts on water reduces the chitosan-water interactions and therefore enhances the chitosan-chitosan interactions. The nontrivial aspect of such a gelation originates essentially from the later polyol-water induced chitosan hydrophobic attractions which are enhanced upon increasing temperature (temperature-controlled gelation). At low temperatures, chitosan-water strong interactions protect the hydrated chitosan macromolecules against aggregations. Removal upon heating of the sheath of water molecules favors and strengthens chitosan-chitosan interactions, and hence induces the macromolecules association. However, the gelation would never occur if the two first attractions (CHITOSAN-CHITOSAN & CHITOSAN-PHOSPHATE) are fully unoperational within the chitosan/organo-phosphate solution. This explains the pH-dependence that still governs the temperature-controlled gelation of chitosan/organo-phosphate systems. Although such CHITOSAN-PHOSPHATE electrostatic attractions are present, the phosphate groups can not be the unique cross-linker agent of chitosan chains due to non-compatible stearic hindrance. This significantly differentiate this gelation mechanism from the pure ionic gelation of chitosan by phosphates or polyphosphates divalent anions. A pure ionic cross-linking would not be temperature-controlled or stimulated.

This type of temperature-controlled pH-dependant gelation is specifically induced by organic mono-phosphate dibasic salt in chitosan solution, however it may be induced as well by other organic salts such as mono-sulfate salts of polyols or sugars, such as polyol-sulfate or sugar-sulfate, or mono-carboxylic acid salts of polyols or sugars. For example, in accordance with the present invention, a chitosan/glucose-1-sulfate solution is expected to gelate so as a chitosan/glucose-1-phosphate solution does.

It is also an aim of the present invention to provide an aqueous chitosan/organo-phosphate solution which can be formed and stored at low temperature (4° C.) and transformed at physiological temperatures into three-dimensional stable chitosan/organo-phosphate gel. It includes nontoxic biocompatible components for mammalian or human environments with both components and processes having low toxicity effects towards living biologicals and preserving the cellular viability. The gel also provides good mechanical/handling performances for long periods of time at the physiological temperature and in physiological aqueous media containing amino-acid, ions and proteins. Chitosan derivatives may be selected as well as to process chitosan/organo-phosphate gels, and comprise N,O-substituents of chitosan.

The expression "organo-phosphates (salt)" refers herein, without limitation, to mono-phosphate dibasic salts of polyols or sugars, such as polyol-phosphate dibasic salts or sugar-phosphate dibasic salts. Organo-sulfates (salt) also refer herein to mono-sulfate salts of polyols or sugars, such as polyol-sulfate salts or sugar-sulfate salts. The preferred organo-phosphate salts may be selected from mono-phosphate dibasic salts of glycerol, including glycerol-2-phosphate, sn-glycerol 3-phosphate and 1-glycerol-3-phosphate salts (alpha-glycerophosphate or beta-glycerophosphate), mono-phosphate dibasic salts of histidinol, acetol, diethylstilbestrol, indoleglycerol, sorbitol, ribitol, xylitol, arabinitol, erythritol, inositol, mannitol, glucitol, palmitoyl-glycerol, linoleoyl-glycerol, oleoyl-glycerol or arachidonoyl-glycerol, and mono-phosphate dibasic salts of fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose, hexose, methylthio-ribose or methylthio-deoxy-ribulose. Other mono-salts of interest (sulfate, carboxylate) may be derived from the same polyols or sugars.

The expression "glycerophosphate or glycerophosphate" refers herein to both alpha-glycerophosphate or beta-glycerophosphate isomers. Alpha-glycerophosphate is undistinctively referred for glycerol-3-phosphate (all optical eniantomers) while beta-glycerophosphate is similarly referred for glycerol-2-phosphate.

The expression "three-dimensional" refers herein to the fact that the polymeric solution is simultaneously gelated and shaped by the mold wherein the solution was initially poured. Gels can be produced in glass or plastic-beakers, dishes, tubes or between two plates so as to obtain any expected shapes.

The expression "in situ gelation" refers herein to the formation of chitosan/organo-phosphate gels by injecting the liquid chitosan/glycerophosphate solution within specific sites of mammalian or human environments, e.g. any tissues (muscles, bone, ligaments, cartilages) and organs. Gelation in situ allows complete and precise filling of tissue defects or body cavities. The gelation of the chitosan/organo-phosphate mixture is induced by the physiological temperature.

The expression "endothermal gelation" refers herein to the thermal mechanism of the chitosan/organo-phosphate solution which enables the solution to gelate upon standing at the desired temperature. Induction of sol to gel transitions of chitosan/organo-phosphate systems requires energy via, for example, the temperature.

The expression "cells or cellular matters" refers herein to living biologicals, such as isolated cells, cellular dispersion, cell aggregates, cell spheroids or cells adhered to solid microspheres particles, that are encapsulated within the chitosan/organo-phosphate gels.

The expression "in situ forming" refers herein to the procedure of administrating the ungelated chitosan/organo-phosphate liquid solution to a body site (e.g. connective tissues, body conduits, articular cavities, fractures, bone defects . . . ), and inducing and ensuring within the body site at the physiological temperature a complete gelation of the polysaccharide solution into a gel.

Formation of Chitosan/organo-phosphate Gels

The selected organo-phosphate salt was herein glycerophosphate, but similar results were reached with other mono-phosphate dibasic salts of polyols or Sugars. Chitosan in powder form is dissolved in an aqueous acidic solution until the occurrence of a clear solution is obtained. The proportion of chitosan varies from 0.5 to 5.0% w/v, preferentially from 1.0 to 3.0% w/v. The pH of the aqueous chitosan solution ranges from 4.5 to 5.5. Aqueous chitosan solutions can be sterilized either by filtration with in-line sterile filters (0.22 micrometer) or by steam-autoclaving (120° C). Sterilization of the chitosan/glycerophosphate gels can not be filtered due to the viscosity or steam-autoclaved due to the thermal sensitivity, but can be performed by gamma-irradiation or reached through strictly sterile procedures. Freshly-prepared aqueous chitosan solutions are stored preferably at low positive temperature (4° C.). Glycerophosphate felt in fine powder form is added to, and dissolved within, the aqueous chitosan solution at a temperatures ranging from 4 to 15° C., preferentially 10° C. When a clear homogeneous chitosan/glycerophosphate aqueous solution with a pH ranging from 6.5 to 7.2 is attained, the said solution is poured into the desired receiver, and hold to appropriate temperature to gel. Glycerophosphate felt in form of aqueous solution may be also used.

Depending on their final pH, the chitosan/glycerophosphate solutions are expected to lead either to thermally reversible or irreversible gel. Reversible gels arise from chitosan/glycerophosphate solutions having a pH comprising between 6.5 and 6.9, while the irreversible gels originate from chitosan/glycerophosphate solutions having a pH above 6.9. The nature of the acid that are used for the acidic chitosan solutions does not influence fundamentally the sol to gel transition of the chitosan/glycerophosphate system. The final pH within a chitosan/glycerophosphate solution is dependent upon the pH of the water/acid solution as well as the chitosan and glycerophosphate concentrations. As chitosan and glycerophosphate are two alkaline components, they tend to increase the pH of the acidic solution wherein they are dissolved. Concentrations in chitosan and glycerophosphate can be balanced to reach the appropriate pH of the chitosan/glycerophosphate solution, while taking into consideration the solubility limit of both components, and particularly the one of chitosan.

Three-dimensional Monolithic Gels

The selected organo-phosphate salt was herein glycerophosphate, but similar results were reached with other mono-phosphate dibasic salts, monosulfate salts or monocarboxylate salts of polyols or sugars. The receiver or mold filled with chitosan/glycerophosphate solution are heated at a temperature ranging from 30 to 60° C., preferentially 37° C. The gelation of chitosan/glycerophosphate solution at 37° C. can be performed within a common cell culture incubator. The solution is maintained at the desired temperature until it turns into a gel after a period which ranges from some days to a week (at 30° C.) to few minutes (at 60° C.). At 37° C., the gelation of chitosan/glycerophosphate solution occurs in 1 hour approximately. Once a three-dimensional chitosan/glycerophosphate gel is formed, the said gel is demolded and washed in distilled water. Chitosan/glycerophosphate gels remain stable and keep their three-dimensional shape even at high temperature, 120° C. (in autoclave).

In Situ Formation of Gels

The selected organo-phosphate salt was herein glycerophosphate, but similar results were reached with other mono-phosphate dibasic salts, monosulfate salts or monocarboxylate salts of polyols or sugars. In situ gelation of the chitosan/glycerophosphate solution can be conducted by dispensing the solution from a hypodermic syringe. If needed, the solution may be pre-gelated (initiate the thermal gelation) by keeping the syringe and chitosan/glycerophosphate solution at desired temperature, ideally 37° C., until the first signs of gelation appear. The ready-to-gel chitosan/glycerophosphate mixture is then administrated so as to fill tissue defects or cavities and complete in situ the gelation process (at 37° C.). Injection of chitosan/glycerophosphate solutions is however limited by the viscosity of the solutions which controls the injectability or extrudability of the solutions. A needle having a gauge of 20 and below are ideal materials for injection of such gel solution. Body cavities and tissue defects act as recipients for the solution, but the liquid materials remain in an open aqueous environment. The conformability and diffusability of the chitosan/glycerophosphate solutions is dependent upon the solution and material properties. Increased viscosity results in formation in situ of more compact and less conformable gels.

Encapsulation of Living Biologicals with Chitosan/glycerophosphate Gels

The selected organo-phosphate salt was herein glycerophosphate, but similar results were reached with other mono-phosphate dibasic salts, monosulfate salts or monocarboxylate salts of polyols or sugars. Living cells or cellular matters were prepared using current cell culture techniques. Cells or cellular matters were incorporated and homogenized at low positive temperatures, ranging from 4 to 20° C., ideally 20° C., into the aqueous chitosan/glycerophosphate solution. The cells or cellular matters loaded with chitosan/glycerophosphate mixtures were poured in the desired dishes or wells and incubated at 37° C. Minimal or supplemented cell culture medium was added to the dishes or wells containing the cells or cellular matters loaded with chitosan/glycerophosphate materials so as to maintain alive and metabolically active the living encapsulated biologicals. Cell culture medium was renewed every 2 days following the formation of the chitosan/glycerophosphate gels.

The viability of cells within the solution and gel is potentially reduced by abnormal osmolarity. Chitosan/glycerophosphate systems have changing osmolarities depending upon the ionic glycerophosphate component. The highest is the glycerophosphate salts content, the highest is the osmolarity of the solution, and the greatest is the impairment for the cell viability. Ideal osmolarity for bioencapsulation would be around 270 to 340 mOsmol/kg. Injection and in situ gelation of chitosan/glycerophosphate materials loaded with living cells or cellular matters can be assessed in a similar way. Cells or cellular matters are introduced at a low positive temperature within the aqueous chitosan/glycerophosphate solutions prior to injection and gelation. There exist a direct relationship between the glycerol-2-phosphate disodium salt content and the osmolarity. To reduce such osmolarity problems, the final pH of the chitosan/glycerophosphate can be adjusted to its desired value while keeping the glycerophosphate content as low as possible. However, a low glycerophosphate content limit must be reached for processing the temperature-controlled pH-dependant gelation.

Therapeutic Use and Other Uses of Chitosan-based Gels

A chitosan/organo-phosphate or organo-sulfate gel as previously described is an ideal material for drug delivery system. Such a in situ gel-like forming vehicle, wherein a solid particulate or water-soluble additive is incorporated prior to the gelation, can be administrated topically, directly to the body site to be treated or diagnosed. Anti-bacterial, anti-fungal, steroidal or non-steroidal anti-inflammatory, anti-cancer, anti-fibrosis, anti-viral, anti-glucoma, miotic and anti-cholinergies, anti-psychotic, anti-histaminic and decongestant, anesthetic and anti-parasitic agents may be incorporated within the composition and gel. In a similar fashion, polypeptides or non-living pharmaceutical agents may be incorporated within the composition or gel for restorative, reconstructive or regenerative purposes.

Living microorganisms, plant cells, animal cells or human cells may be entrapped identically within the polysaccharide gel by introduction prior to the gelation. The cells or micro-organisms loaded gels may be applied to biotechnological purposes in medicine or in other industrial areas. Chitosan-based in situ forming gels can be formed subcutaneously, intramuscularly, intra-peritoneally or within biological connective tissues, bone defects, fractures, articular cavities, body conduits or cavities, eye cul-de-sac, solid tumor vasculatures, etc. . .

The present invention will be more readily understood by referring to the following examples which are given to illustrate the invention rather than to limit its scope.

EXAMPLE I
Typical Gelation of a Chitosan/organo-phosphate System

Experiment 1

Typical experiment was carried out by dissolving 0.2 g of chitosan in 10 ml of aqueous acetic acid solution (0.1M). The pH of the acetic acid solution has been beforehand adjusted to 4.0 by adding droplets of potassium hydroxide solution (1M). The 2% (w/v) chitosan solution so obtained had a pH of about 5.6. Then, 0.800 g of glycerophosphate disodium salt pentahydrate were added to and dissolved in the chitosan solution at 10° C. The pH of the resulting homogeneous liquid mixture become 7. This mixture was disposed in a glass scintillation vial in the incubator at 37° C. for 2 hours, enough time to achieve bulk-gelation process. The resulting bulk gel was immersed in renewed baths of distilled water in order to remove the excess of glycerophosphate salt.

A similar result was reached when the glycerophosphate disodium salt (or glycerol-2-phosphate disodium salt) was replaced by the alpha-glycerophosphate disodium salt (or glycerol-3-phosphate disodium salt).

Experiment 2

A homogenized chitosan/glycerophosphate solution was prepared as in Experiment 1 and disposed in a dual gel caster having a glass plates gel sandwich with a 1.6 mm interspaces, and the system was kept in an oven at 37° C. The formation of a gel membrane was reached within 2 hours and the membrane was unmolded from the gel caster.

Experiment 3

A 0.110 g of fumed silica under solid particle form (AEROSIL) was dispersed within a solution prepared by dissolving 0.200 g of chitosan in 10 ml of aqueous acetic acid solution. . A 0.800 g of glycerophosphate disodium salt pentahydrate was added to the chitosan-silica dispersion. The resulting composition was disposed in a glass scintillation vial in water bath kept at 37° C. The gelation of the chitosan/glycerophosphate component was observed within 2 hours, and the chitosan/glycerophosphate gel includes dispersed solid silica particles.

Experiment 4

A 0.200 g of chitosan was dissolved in acetic acid solution as in Experiment 1. A 1.239 g of glucose-1-phosphate disodium salt tetrahydrate was added and dissolved so as to reach a clear chitosan/glucose-1-phosphate solution. This chitosan/glucose-1-phosphate solution placed in a glass scintillation vial was maintained at 37° C. The Sol to Gel transition occurs at 37° C. within 3 hours. The resulting bulk gel was immersed in renewed baths of distilled water in order to remove the excess of glucose-phosphate salt.

The experiment was conducted as described in Experiment 4 except that the 1.239 g of glucose-1-phosphate salt was replaced by 0.100 g of fructose-6-phosphate disodium salt dihydrate.

EXAMPLE II
Effect of Composition on pH of Solution and Occurrence of Gelation A mother acidic solution made of a Water/Acetic acid was prepared for all experiments. The pH of this mother acidic solution was adjusted to 4.0. High molecular weight (M.w. 2,000,000) Chitosan powder was added and dissolved in a volume of the mother acidic solution so as to produce Chitosan solutions having Chitosan proportions ranging from 0.5 to 2.0% w/v (Table 1). Table 1 reports the measured pH for the different samples.

TABLE 1

| Chitosan Aqueous Solutions and pH levels | | | | |
|---|---|---|---|---|
| Chitosan conc. (w/v) | 0.5 | 1.0 | 1.5 | 2.0 |
| pH of Chitosan Sol. | 4.68 | 4.73 | 5.14 | 5.61 |

Glycerophosphate was added to the chitosan solutions and induces a pH increase. Table 2 shows the effect of glycerophosphate concentration on different chitosan solution. The concentration of glycerophosphate ranges from 0.065 to 0.300 mol/L. The chitosan/glycerophosphate solutions in glass vials were maintained at 60 and 37° C., and bulk and uniform gelation was noted within 30 minutes at 60° C. and 6 hours at 37° C. (Table 2 and FIG. 1). Chitosan and beta-glycerophosphate components individually influence the pH increase within the aqueous solutions, and consequently influence the Sol to Gel transition. As well as the dissolved materials, the initial pH of the mother water/acetic acid solution would also influence the Sol to Gel transition, but this potential effect seems to be limited by the counteraction of the chitosan solubility which depends on the pH of the solution.

TABLE 2

Gelation of Chitosan/Glycerophosphate Compositions

| Chitosan conc. (w/v) | | 1.5 | | | 2.0 | |
|---|---|---|---|---|---|---|
| pH of Chitosan Sol. | | 5.14 | | | 5.61 | |
| GP conc. (mol/L) | 0.130 | 0.196 | 0.260 | 0.130 | 0.196 | 0.260 |
| pH of Chitosan-GP Sol. | 6.64 | 6.83 | 6.89 | 6.78 | 6.97 | 7.05 |
| Gelation | | | | | | |
| 60° C. | <30 min. | <30 min. | <30 min. | <30 min. | <30 min. | <30 min. |
| 37° C. | No | No | No | No | <6 hrs | <6 hrs |

EXAMPLE III
Thermal Reversibility of Gelation of Chitosan/glycerophosphate Systems A first chitosan/glycerophosphate solution was prepared from a 10 ml of mother water/acetic acid solution of pH 4.0 by adding and dissolving 0.200 g of chitosan and 0.800 g of glycerophosphate disodium salt pentahydrate. The resulting chitosan/glycerophosphate solution has a pH about 7.05 and is heated at 60° C. where it gels rapidly. The chitosan/glycerophosphate gel is cooled at a temperature about 0–4° C., but no transition is observed with time and the gel remains stable at 4° C. This chitosan/glycerophosphate gel is thermo-irreversible.

A second chitosan/glycerophosphate solution was prepared from a 10 ml of mother water/acetic acid solution of pH 4.0 by adding and dissolving 0.100 g of chitosan and 0.800 g of glycerophosphate disodium salt pentahydrate. The chitosan/glycerophosphate solution has a pH about 6.78 and is heated at 60° C. for gelation. The resulting chitosan/glycerophosphate gel is then cooled at a temperature about 0–4° C., and a Gel to Sol transition is observed after a period of time. The gel returns to a liquid solution at low positive temperatures, for instance at 4° C. When this solution is reheated at 60° C., the reverse mechanism (Sol to Gel transition) appears again and a gel re-forms. The Sol to Gel to Sol transition is reproducible between temperatures at 4 and 60° C. This chitosan/glycerophosphate gel is thermoreversible. The thermo-reversibility of the Sol to Gel transition of the chitosan/glycerophosphate systems is found to be predominantly dependant on the pH of the chitosan/glycerophosphate solution. An example of pH and observed reversibility is give in Table 3. Experimental observations on chitosan/glycerophosphate systems have shown that thermal reversibility of the Sol to Gel mechanism changes at a pH of the chitosan/glycerophosphate solutions in the vicinity of 6.9. A reversible gelation of chitosan/glycerophosphate solutions occurs when the pH is comprised between 6.5 and 6.9. A very similar result was observed with other monophosphate dibasic salts of polyols or sugars such as glucose-1-phosphate salts.

TABLE 3

Effect of pH on Sol to Gel Reversibility for a 2.0% w/v Chitosan Concentration

| GP conc. (mole/L) | 0.130 | 0.163 | 0.196 | 0.260 |
|---|---|---|---|---|
| pH of Chitosan-GP Sol: | 6.78 | 6.87 | 6.97 | 7.05 |
| Reversibility of Sol to Gel 4° C.–60° C. | Reversible, Cycle | Reversible, Cycle | Irreversible | Irreversible |

EXAMPLE IV
In situ Gelation of Chitosan/glycerophosphate Materials

Adult New-Zealand White rabbits were anesthetized by intra-venous administration of Sodium Pentosorbital (1 ml/kg) and maintained under anesthesia for 3 hours. After 3 hours, the animals were sacrificed by anesthetic overdose and the experiments were continued post-mortem. The animal was maintained on the back, and the localized zones of the upper limbs and torso region were shaved. The skin was incised so as to free the sub-cutaneous fibrous membranes and muscle of the limb.

Two chitosan/glycerophosphate solutions were prepared previously, disposed in hypodermic syringes and maintained at a low temperature (4–10° C.): the solution I was a 2.7 % w/v low M.w. chitosan and 9.0 % w/v glycerophosphate while the solution II was a 2.5% medium M.w. chitosan and 9.0% w/v glycerophosphate. Syringes were equipped with No. 21 gauge needles. The chitosan/glycerophosphate solutions were not prepared or kept under strict sterile conditions since the animal experiments were performed within a period of time about 4–5 hours. A volume (a) of 1.0–1.5 ml of the solution I was injected sub-cutaneously within the fibrous membranes while a second volume (b) of 2.0 ml of the solution I was injected through the knee-joint capsule into the articular cavity. A volume (c) of 1.0 ml of the solution II was injected sub-cutaneously at the torso region. All injection sites were recovered with the excised tissues where necessary. The gelation in situ was allowed for a period of 3 hours, then the sites were re-opened or excised and the in situ formed gels were collected.

TABLE 4

Injections and formation in situ of Gels

| | [chitosan] % w/v | Volume | Remarks |
|---|---|---|---|
| Subcutaneous, Legs. | 2.7 | 1.5 | Gel expands and conforms to the tissue surface. |
| Intraarticular, Knee joint | 2.7 | 2.0 | Gel expands and conforms to the joint volume contour. |
| Subcutaneous, Torso | 2.5 | 1.0 | Gel does not expand and retains its drop shape. |

EXAMPLE V
Encapsulation of Mammalian Cells

A 2.5% w/v chitosan aqueous solution was prepared as previously described. A 1.98 g of the chitosan solution was admixed with 0.18 g of beta-glycerophosphate disodium salt, 0.4 ml of Dubelcco Modified Eagle Medium F12 wherein animal chondrocytes are dispersed, and 0.2 ml of Dubelcco Modified Eagle Medium F12. Chondrocytes were isolated from calf shoulder cartilage surfaces and collected from primary monolayer cultures. Dubelcco Modified Eagle Medium F12 comprises dexamethasone, ascorbic acid and 10% fetal bovine serum. All Chitosan solutions, chitosan/glycerol-2-phosphate solutions and procedures were sterile. Once the chondrocytes in chitosan/glycerol-2-phosphate dispersion is casted, it is placed in an incubator at 37° C. until the gelation. Gelation of chitosan/glycerol-2-phosphate system is observed within 2 hours. Viability tests on such chondrocytes-loaded chitosan/glycerol-2-phosphate gels indicate a range from 10% to 70% of alive chondrocytes. Encapsulation of micro-organisms, plant cells, animal cells or human cells within chitosan/glycerol-2-phosphate gels can be performed with changing properties depending the expected viability.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A polysaccharide based gel solution which comprises:
   a) 0.1 to 5.0% by weight of chitosan; and
   b) 1.0 to 20% by weight of a salt of polyol or sugar selected from the group consisting of monophosphate dibasic salt of polyol or sugar;
   wherein said gel solution is a solution at pH between 6.5 and 7.4 at a temperature below 20° C., and forms a gel within a temperature range from 20 to 70° C.

2. A gel solution according to claim 1, wherein said salt is a mono-phosphate dibasic salt of glycerol selected from the group consisting of glycerol-2-phosphate salts, sn-glycerol 3-phosphate salts and L-glycerol-3-phosphate salts.

3. A gel solution according to claim 1, wherein said salt is a mono-phosphate dibasic salt of polyol selected from the group consisting of histidinol, acetol, diethylstilbestrol, indole-glycerol, sorbitol, ribitol, xylitol, arabinitol, erythritol, inositol, mannitol, glucitol and a mixture thereof.

4. A gel according to claim 1, wherein said salt is a mono-phosphate dibasic salt and said sugar is selected from the group consisting of fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose. hexose, methylthio-ribose, methylthio-deoxy-ribulose, and a mixture thereof.

5. A gel solution according to claim 1, wherein said salt is a mono-phosphate dibasic salt of polyol selected from the group consisting of palmitoyl-glycerol, linoleoyl-glycerol, oleoyl-glycerol, arachidonoyl-glycerol, and a mixture thereof.

6. A gel solution according to claim 1, wherein said gel solution is selected from the group consisting of chitosan-β-glycerophosphate, chitosan-α-glycerophosphate, chitosan-glucose-1-glycerophosphate, and chitosan-fructose-6-glycerophosphate.

7. A gel solution according to claim 1, wherein solid particulate or water-soluble additives are incorporated within said polysaccharide gel prior to gelation.

8. A gel solution according to claim 1, wherein drugs, polypeptides or non-living pharmaceutical agents are incorporated within said polysaccharide gel prior to gelation.

9. A gel solution according to claim 1, wherein living microorganisms, plant cells, animal cells or human cells are encapsulated within said polysaccharide gel prior to gelation.

10. A method for producing a solution of a polysaccharide based gel according to claim 1, which comprises the steps of:
    a) dissolving a chitosan within an aqueous acidic solution of a pH from about 2.0 to about 5.0 to obtain an aqueous polysaccharide composition having a concentration of 0.1 to 5.0% by weight of a chitosan;
    b) dissolving 1.0 to 20% by weight of a salt of polyol or sugar, wherein said salt is selected from the group consisting of mono-phosphate dibasic salt, in said aqueous polysaccharide composition of step a) to obtain a solution of said polysaccharide based gel, wherein said solution of the polysaccharide based gel has a concentration of 0.1 to 5.0% by weight of a chitosan, and a concentration of 1.0 to 20% by weight of a salt of a polyol or sugar, and said solution of the polysaccharide based gel has a pH from about 6.5 to about 7.4.

11. The method of claim 10, wherein a pharmaceutical agent is added to the polysaccharide gel solution of step b).

12. The method of claim 10, wherein said aqueous acidic solution is prepared from organic or inorganic acids selected from the group consisting of acetic acid, ascorbic acid, salicylic acid, phosphoric acid, hydrochloric acid, propionic acid, formic acid, and a mixture thereof.

13. The method of claim 10, wherein said salt is a mono-phosphate dibasic salt of glycerol, wherein said glycerol is selected from the group consisting of glycerol-2-phosphate, sn-glycerol 3-phosphate and L-glycerol-3-phosphate salts.

14. The method of claim 10, wherein said salt is a selected from the group consisting of glycerophosphate disodium, glycerophosphate dipotassium, glycerophosphate calcium, glycerophosphate barium and glycerophosphate strontium.

15. The method of claim 10, wherein said salt is a mono-phosphate dibasic salt of a polyol, and said polyol is selected from a group comprising histidinol, acetol, diethylstilbestrol, indoleglycerol, sorbitol, ribitol, xylitol, arabinitol, erythritol, inositol, mannitol, glucitol, and a mixture thereof.

16. The method of claim 10, wherein said salt is a mono-phosphate dibasic salt of a sugar, and said sugar is selected from a group comprising fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose, hexose, methylthio-ribose, methylthio-deoxy-ribulose, and a mixture thereof.

17. The method of claim 10, wherein said salt is a mono-phosphate dibasic salt of a polyol, and said polyol is selected from the group consisting of palmitoyl-glycerol, linoleoyl-glycerol, oleoyl-glycerol, arachidonoyl-glycerol, and a mixture thereof.

18. The method of claim 10, wherein said salt is a mono-phosphate dibasic salt and said phosphate is selected from the group consisting of a phosphate disodium, phosphate dipotassium, phosphate calcium, phosphate barium and phosphate strontium.

19. The method of claim 10, wherein the molecular weight of chitosan is ranging from about 10,000 to 2,000,000 Da.

20. The method of claim 10, wherein the polysaccharide gel is thermoirreversible or thermoreversible by adjusting the polysaccharide gel pH.

21. The method of claim 20, wherein polysaccharide gel is thermoirreversible when the pH of said polysaccharide gel solution is >6.9.

22. The method of claim 20, wherein polysaccharide gel is thermoreversible when the pH of said polysaccharide gel solution is <6.9.

23. The method of claim 10, wherein solid particulate additives are added to the polysaccharide gel solution of step b).

24. A method for producing a polysaccharide based gel, which comprises the steps of:
  a) dissolving a chitosan within an aqueous acidic solution of a pH from about 2.0 to about 5.0 to obtain an aqueous polysaccharide composition having a concentration of 0.1 to 5.0% by weight of a chitosan;
  b) dissolving 1.0 to 20% by weight of a salt of polyol or sugar, wherein said salt is selected from the group consisting of mono-phosphate dibasic salt, in said aqueous polysaccharide corn position of step a) to obtain a solution of said polysaccharide based gel, and wherein said solution of the polysaccharide based gel has a pH from about 6.5 to about 7.4; and
  c) heating said polysaccharide gel solution to a temperature ranging from about 20° C. to about 80° C. to result in formation of a polysaccharide gel.

25. The method of claim 24, which further comprises between steps b) and c) the following step,
  b1 dispensing for gelation the polysaccharide gel solution into a receiver, either in a mold or within a tissue, organ or body cavity.

26. The method of claim 25, wherein said polysaccharide gel solution is introduced within an animal or human body by injection or endoscopic administration, and gelled in situ at a temperature of about 37° C.

27. The method of claim 24, wherein said temperature ranges from about 37° C. to about 60° C.

28. The method of claim 27, wherein said temperature is about 37° C.

* * * * *